United States Patent
Marshall

(10) Patent No.: US 6,997,936 B2
(45) Date of Patent: Feb. 14, 2006

(54) SKIN PRICKER BLOOD SAMPLING DEVICE

(75) Inventor: Jeremy Marshall, Jericho (GB)

(73) Assignee: Owen Mumford Limited, Oxford (GB)

( * ) Notice: Subject to any disclaimer, the term of this patent is extended or adjusted under 35 U.S.C. 154(b) by 181 days.

(21) Appl. No.: 10/257,870

(22) PCT Filed: Feb. 15, 2002

(86) PCT No.: PCT/GB02/00681

§ 371 (c)(1),
(2), (4) Date: Feb. 10, 2003

(87) PCT Pub. No.: WO02/065909

PCT Pub. Date: Aug. 29, 2002

(65) Prior Publication Data

US 2004/0102802 A1    May 27, 2004

(30) Foreign Application Priority Data

Feb. 17, 2001    (GB) .................................... 0103973

(51) Int. Cl.
*A61B 17/32* (2006.01)
(52) U.S. Cl. ...................... 606/181; 606/182; 606/183; 606/184
(58) Field of Classification Search ................ 606/181, 606/182, 184, 185, 167, 183, 188; 604/110
See application file for complete search history.

(56) References Cited

U.S. PATENT DOCUMENTS

| 4,388,925 | A | * | 6/1983  | Burns ........................ 606/182 |
| 4,817,603 | A |   | 4/1989  | Turner et al. |
| 5,487,748 | A |   | 1/1996  | Marshall et al. |
| 5,611,809 | A |   | 3/1997  | Marshall et al. |
| 5,707,384 | A | * | 1/1998  | Kim ........................... 606/181 |
| 5,741,288 | A | * | 4/1998  | Rife ............................ 606/181 |
| 6,106,537 | A | * | 8/2000  | Crossman et al. .......... 606/181 |
| 6,136,013 | A | * | 10/2000 | Marshall et al. ............ 606/167 |
| 6,149,608 | A |   | 11/2000 | Marshall et al. |
| 6,258,112 | B1|   | 7/2001  | Schraga |
| 6,390,990 | B1| * | 5/2002  | Marshall et al. ............ 600/573 |
| 6,719,771 | B1| * | 4/2004  | Crossman ................... 606/181 |

* cited by examiner

*Primary Examiner*—Glenn K. Dawson
*Assistant Examiner*—Michael G. Mendoza
(74) *Attorney, Agent, or Firm*—Young & Thompson

(57) ABSTRACT

A skin pricker has a housing (1) for a lancet (5) which, when released from a rearward cocked position, is propelled forwards by a spring momentarily to project its tip (3). During the forward motion a peg (12) within the housing (1) passes along a slot (10) in the lancet and, just before the tip (3) projects, snaps through a neck (11) at the rear end of the slot. If the lancet (5) is then pushed back, the peg (12) cannot re-enter the slot (10): instead it wedges the lancet sideways and, before it can be re-cocked, traps the lancet behind an abutment (13) ensuring that the tip (3) cannot be re-exposed.

11 Claims, 3 Drawing Sheets

SKIN PRICKER BLOOD SAMPLING DEVICE

Figure 1:
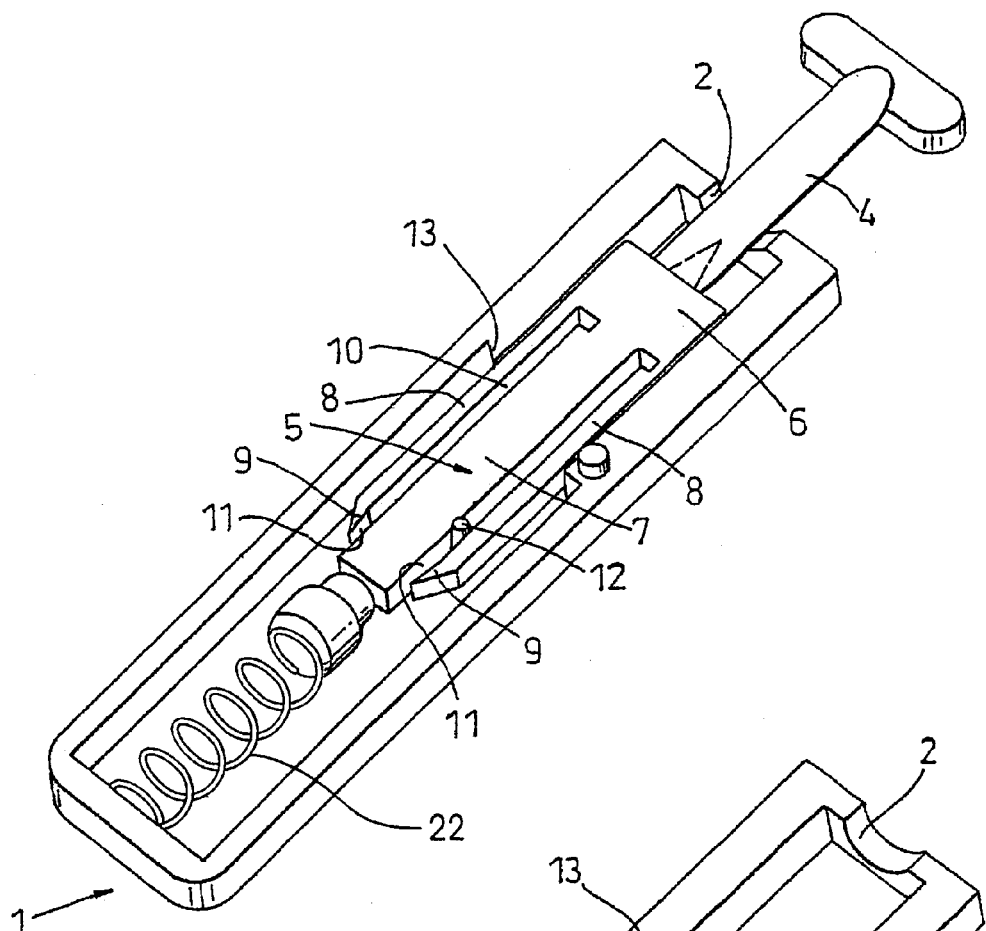

This invention relates to skin prickers. It is concerned with skin prickers of the kind where a lancet is pushed back in its housing to a cocked position where it is held against a compressed spring. When the lancet is released the needle tip momentarily projects and the bounce-back of the lancet withdraws it into the housing. Arrangements are made to prevent the lancet being fired again, so that it is a single use device and has to be discarded.

The aim of this invention is to simplify the structure by which this re-use is prevented.

According to the present invention there is provided a skin pricker comprising an elongate housing, a lancet within the housing, spring urged towards the forward end thereof, means for releasing the lancet along a firing path from a cocked rearward position to cause momentary projection of its needle tip through an aperture at said forward end, and means for preventing re-exposure of the tip after such momentary projection, characterised in that the preventing means includes a projection on the interior of the housing which initially co-operates with a longitudinal channel in the lancet having a non-return rear end for escape of the projection from the channel as the lancet tip approaches exposure, subsequent co-operation of the projection with the lancet if re-cocking is attempted causing the lancet to be misaligned from the firing path.

Conveniently, the channel is formed by the gap between the main body of the lancet and a spring finger carried by the body and extending rearwardly alongside it, the rear end of the finger converging towards said body to form a neck through which the projection can snap.

Preferably, there will be two fingers symmetrically disposed one on either side of the body, one finger to co-operate with the projection and the other being redundant. It will then not matter which of either of two ways the lancet is assembled with the housing.

The interior of the housing may have an abutment behind which the lancet is engaged when misaligned. If it is pushed back towards the cocked position after firing, the projection acting on the outside of the finger will urge the lancet sideways, and although the lancet may be re-cocked, if re-fired it will be blocked by the abutment.

The arrangement could be reversed, with the projection on the lancet and the channel in the housing with its non-return end being the forward end thereof.

Preferably, a removable cap initially shrouds the tip of the lancet and extends through the aperture. It can serve as a means by which the lancet can be pushed back along the firing path from an assembled position with its needle within the housing to the cocked position.

Another desirable feature is to have a trigger carried by the housing with two modes of engagement with the lancet. In the first mode it can restrain the lancet from significant forward movement from the assembled position but allow the pushing back of the lancet, and in the second mode it will hold the lancet in said cocked position until operation of the trigger releases it.

Conveniently, the lancet has a ratchet type engagement with the trigger, snapping back past a tooth on the trigger as it reaches the cocked position. This tooth can also serve as the first mode restraint, co-operating with a projection on the lancet to stop the lancet moving forwards but, when the trigger is operated to fire the lancet, being lifted clear of the lancet so as not to obstruct said projection as the lancet moves forward.

Figure 2:
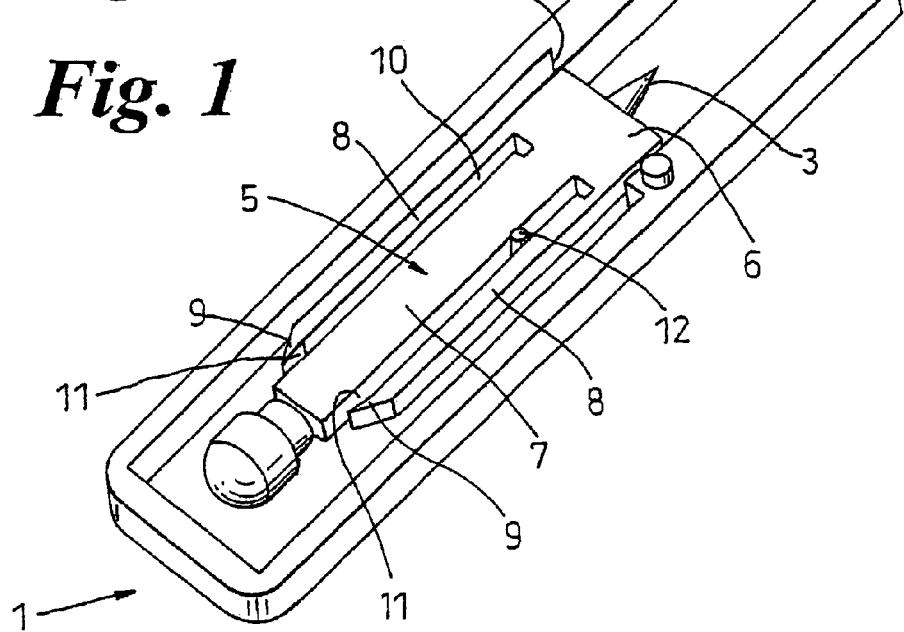
Figure 3:
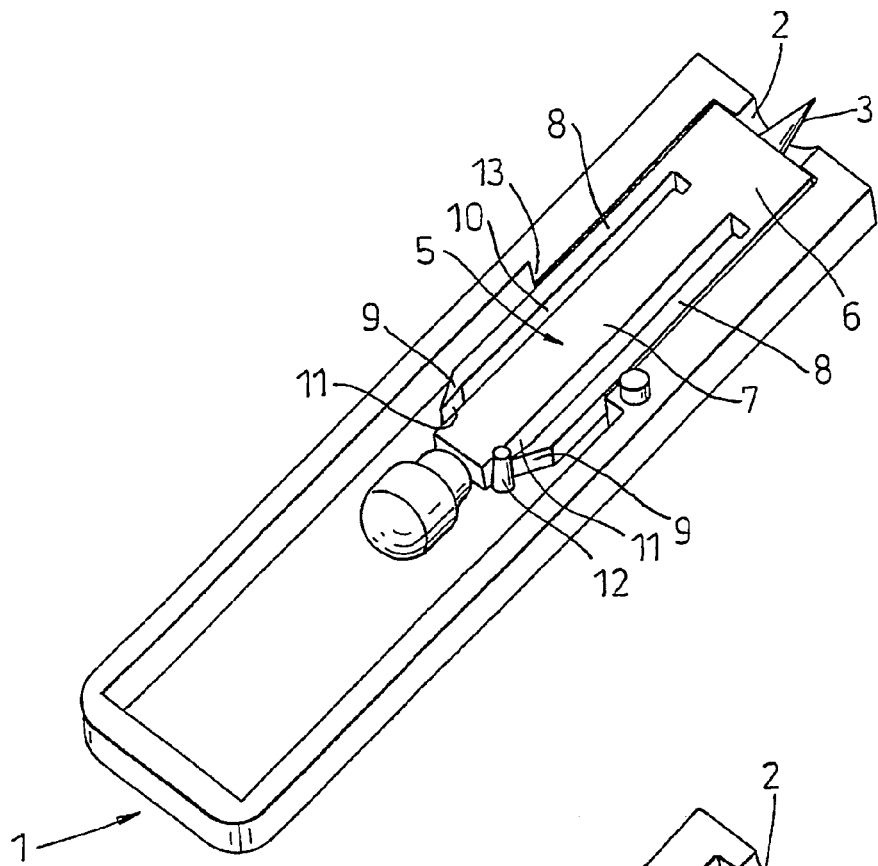
Figure 4:
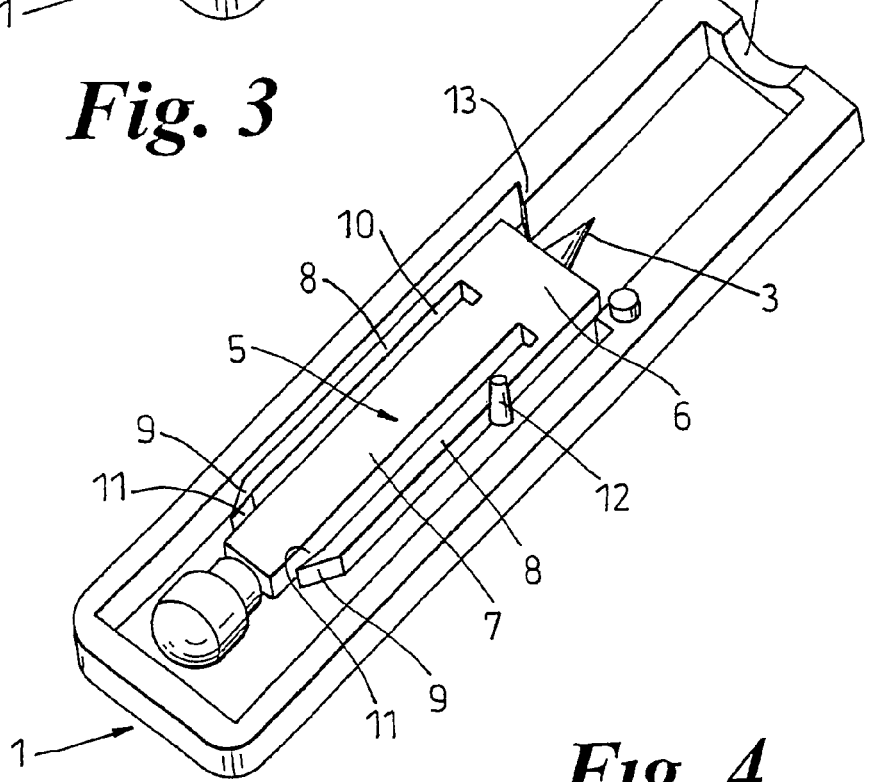
Figure 5:
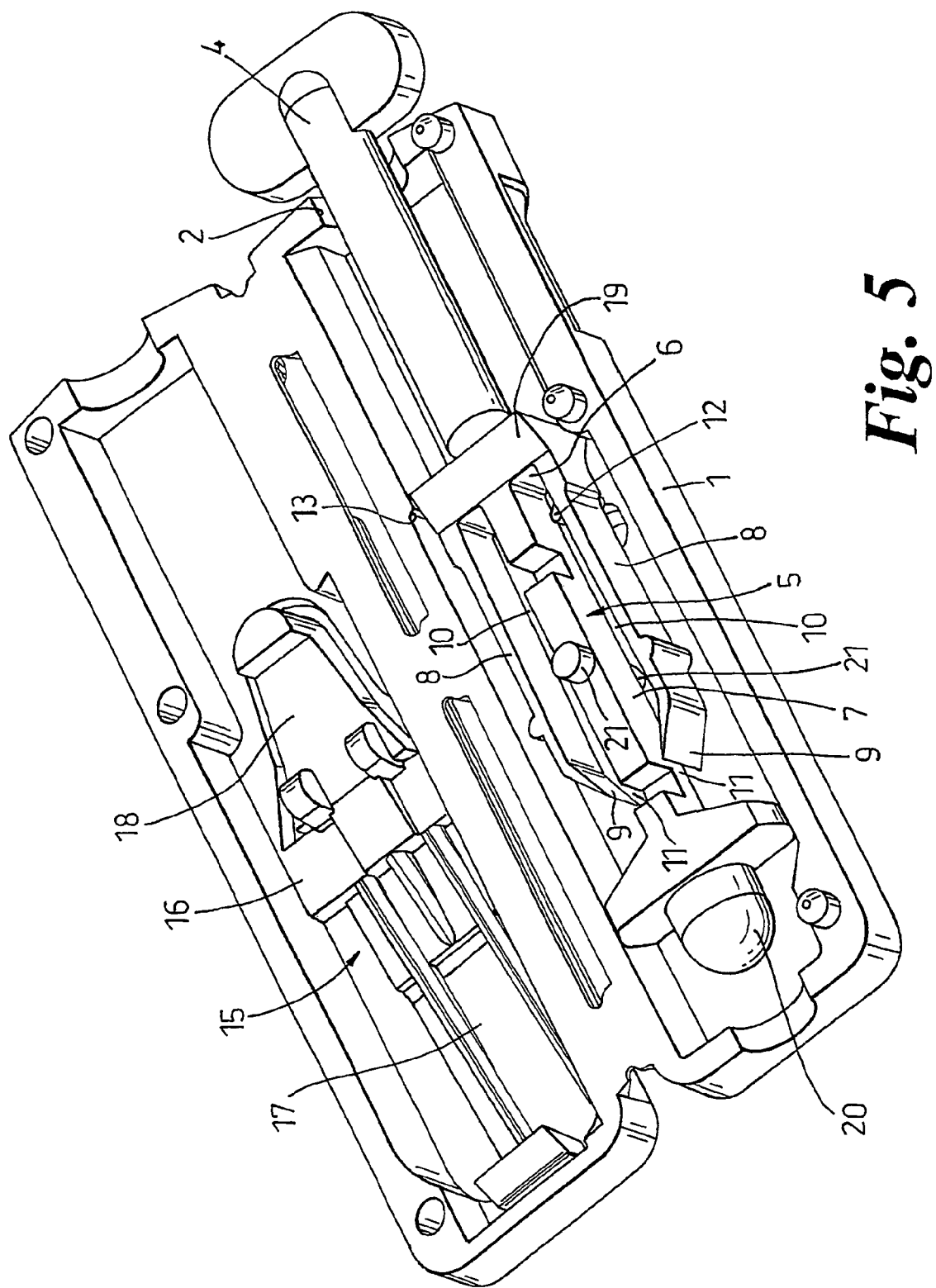

For a better understanding of the invention, one embodiment will now be described, by way of example, with reference to the accompanying drawing, in which:

FIG. 1 is a diagrammatic perspective view of half a skin pricker housing with a lancet as initially assembled therein, FIG. 2 is a similar view but showing the lancet cocked, FIG. 3 is a similar view but showing the lancet fired, FIG. 4 is a similar view but showing the lancet re-cocked but immobilised after firing, and FIG. 5 is a perspective view of a complete skin pricker, opened out and with the lancet in the cocked position.

The housing half 1 of the pricker of FIGS. 1 to 4 is a shallow, elongated rectangular open-topped box, the housing being completed by a complementary half (not shown) closed over it. At one end there is a semi-circular recess 2, matched by another one in the other half to create an aperture through which the tip of a lancet needle will momentarily project. Initially that tip 3 is shrouded by a needle cap 4 integrally moulded with a lancet body 5 which can move longitudinally within the housing.

The body 5 is an elongated T-shaped block the cross portion 6 being at the forward end and the stem 7 housing most of the needle. Alongside the stem, on each side, there is a finger 8 extending back from the rear corners of the cross-portion 6 to terminate in tapered, inwardly inclined tips 9. These create slots 10 which narrow at necks 11 at the rear ends.

The interior of the half 1 has an upstanding peg 12 positioned offset to one side of the longitudinal centre line so that, when the lancet is inserted, it lies within one of the slots 10, near its rear end. The cross portion 6 lies within a narrowed part of the housing which guides the lancet during cocking and firing. At this stage the needle tip 3, still within the cap 4, is within the housing. On the other side of the half 1, where the narrowed part terminates, the wall provides an undercut shoulder 13 forward of the peg 12.

With the housing complete, when the pricker is to be used the lancet is pressed back using the cap 4. It will be captured in the cocked position of FIG. 2 by a trigger mechanism (not shown). A spring 22, shown only in FIG. 1 for clarity of illustration, acting between the rear end of the housing and the free end of the stem 7 will then be fully compressed and the peg 12 is now towards the forward end of the slot 10.

On release, the lancet shoots forward, beyond its assembled position. When the finger tip 9 reaches the peg 12, the latter snaps through the associated neck 11 and the FIG. 3 position is reached, with the needle tip 3 projecting.

The lancet will bounce back into a safe position with the needle tip 3 just inside the housing but will be arrested by the peg 12 meeting the inclined outer face of the finger tip 9, tending to wedge the associated finger 8 in towards the stem 7. Obviously, it cannot be re-fired in that position. However, it can be re-cocked but, as it is pushed back, the peg 12, acting now on the outside of the finger 8, pushes the lancet towards the other side. The finger is fairly stiff, and as the peg approaches its root it deflects more and more and pressure on the lancet increases. So once the cross portion 6 passes the shoulder 13, the lancet is shifted sideways with a sudden snap to bring the corner of that portion 6 behind the shoulder 13 while the finger 8 straightens out, as shown in FIG. 4. The lancet may then be re-cocked, but if re-fired it will not get past the shoulder 13.

It will thus be seen that re-use of the pricker is prevented.

FIG. 5 shows a complete pricker, opened out and with the lancet in the position of FIG. 2 but with its cap still in place. The same references are used to indicate the parts equivalent to those of FIGS. 1 to 4.

The now visible complementary half 14 differs primarily from the half 1 in having the trigger mechanism 15 previously referred to. This is of the rocker type, with an intermediate transverse web 16 carrying to the rear a longitudinal arm 17 inclining slightly proud of the half 14 and to the front an inwardly hooked section 18. This will snap over and catch a tooth 19 integrally formed with the portion 6 when the lancet is pushed back to the cocked position. The tooth 19 is duplicated on the other side of the portion 6 for the same reason the arms 8 are duplicated, while the spring 22 locates onto a knob 20 at the rear end of the lancet body 5. With the lancet in the cocked position shown, when the arm 17 is pressed flush with the half 14, twisting the web 16, the lancet is released and shoots forward.

The stem 7 of the lancet body has two opposed studs 21 at about its mid-length, one of which projects towards the trigger, the other being spare in case the lancet is fitted the other way up. Initially the stud 21 will be immediately behind the hook of the trigger portion 18 and so if the user pulls the cap 4 instead of pushing it, the lancet cannot move any significant distance forwards, and certainly not far enough to allow the peg 12 to escape through its associated neck 11. If it did that, it would not be possible to fire the lancet properly. So the stud 21 is a safety measure against the device being made prematurely inoperative.

The stud 21 will travel just beyond the hooked section 18 when the lancet is fired, but so rapid is the movement that the user will not have time to release the arm 17 and cause the hook to engage the stud 21 as the lancet shoots forwards. The lancet will have bounced back to its initial position before the trigger assumes its original attitude.

This feature forms the main subject of our co-pending International Application claiming priority from British Patent Application No. 0103977.5.

What is claimed is:

1. A skin pricker comprising an elongate housing having an interior and forward and rearward ends, a lancet within the housing, spring urged towards the forward end thereof, means for releasing the lancet along a firing path from a cocked rearward position to cause momentary projection of its needle tip through an aperture at said forward end, and means for preventing re-exposure of the tip after such momentary projection, characterised in that the preventing means includes a projection on the interior of the housing or on the lancet which initially co-operates with a longitudinal channel in the lancet or on the housing having a non-return rear end for escape of the projection from the channel as the lancet tip approaches exposure, subsequent co-operation of the projection with the lancet if re-cocking is attempted causing the lancet to be misaligned from the firing path.

2. A skin pricker as claimed in claim 1, characterised in that the channel is formed by a gap between a main body portion of the lancet and a spring finger carried by the body and extending rearwardly alongside it, the rear end of the finger converging towards said body to form a neck through which the projection can snap.

3. A skin pricker as claimed in claim 2, characterised in that there are two fingers symmetrically disposed one on either side of the body, one finger to co-operate with the projection and the other being redundant.

4. A skin pricker as claimed in claim 1, characterized in that the interior of the housing has an abutment behind which the lancet is engaged when misaligned.

5. A skin pricker as claimed in claim 1, characterized in that the projection is on the lancet and the channel is in the housing with its non-return end being the forward end thereof.

6. A skin pricker as claimed in claim 1, characterized in that a removable cap initially shrouds the tip of the lancet and extends through the aperture, and also serves as a means by which the lancet can be pushed back along the firing path from an assembled position with its needle within the housing to the cocked position.

7. A skin pricker as claimed in claim 1, characterized in that a trigger is carried by the housing with two modes of engagement with the lancet, in the first mode restraining the lancet from significant forward movement from the assembled position but allowing the pushing back of the lancet, and in the second mode holding the lancet in said cocked position until operation of the trigger releases it.

8. A skin pricker as claimed in claim 7, characterised in that the lancet has a ratchet type engagement with the trigger, snapping back past a tooth on the trigger as it reaches the cocked position.

9. A skin pricker as claimed in claim 8, characterised in that said tooth also serves as the first mode restraint, co-operating with a projection on the lancet to stop the lancet moving forwards but, when the trigger is operated to fire the lancet, being lifted clear of the lancet so as not to obstruct said projection as the lancet moves forwards.

10. A skin pricker as claimed in claim 2, characterized in that the interior of the housing has an abutment behind which the lancet is engaged when misaligned.

11. A skin pricker as claimed in claim 3, characterised in that the interior of the housing has an abutment behind which the lancet is engaged when misaligned.

* * * * *